United States Patent [19]
Nicolai et al.

[11] Patent Number: 5,972,950
[45] Date of Patent: Oct. 26, 1999

[54] 1,2-DIARYLMETHYLENE DERIVATIVES, THEIR METHODS OF PREPARATION AND THEIR USES IN THERAPEUTICS

[75] Inventors: Eric Nicolai, Rueil Malmaison; Jean-Marie Teulon, La Celle Saint Cloud, both of France

[73] Assignee: Laboratories UPSA, Agen, France

[21] Appl. No.: 08/939,743

[22] Filed: Oct. 6, 1997

Related U.S. Application Data

[63] Continuation-in-part of application No. 08/822,842, Mar. 24, 1997, Pat. No. 5,840,753.

[30] Foreign Application Priority Data

Oct. 8, 1996 [FR] France ..................................... 96 12234

[51] Int. Cl.$^6$ .......................... A61K 31/44; A61K 31/38; C07D 213/55; C07D 333/16
[52] U.S. Cl. .......................... 514/277; 514/302; 514/345; 514/438; 514/443; 514/446; 546/115; 546/342; 546/301; 549/32; 549/66; 549/80
[58] Field of Search ................................. 549/434, 32, 80, 549/66; 562/468; 560/11, 12; 514/277, 302, 345, 446, 115, 301, 342

[56] References Cited

U.S. PATENT DOCUMENTS 5,807,873  9/1998  Nicolai et al. ........................... 514/336

*Primary Examiner*—Alan L. Rotman
*Attorney, Agent, or Firm*—Barry J. Marenberg

[57] ABSTRACT

The present invention relates to the derivatives of formula:

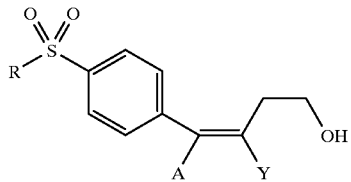

and to their use in therapeutics, especially as drugs with anti-inflammatory and analgesic properties.

9 Claims, No Drawings

1,2-DIARYLMETHYLENE DERIVATIVES, THEIR METHODS OF PREPARATION AND THEIR USES IN THERAPEUTICS

CROSS REFERENCE TO RELATED APPLICATION

This is a continuation-in-part application of U.S. Ser. No. 08/822,842 filed on Mar. 24, 1997, now U.S. Pat. No. 5,840,753.

The present invention relates to the 1,2-diarylmethylene derivatives of general formula (I) below and their addition salts, particularly pharmaceutically acceptable addition salts, as novel products.

One of the arachidonic acid biotransformation pathways is the cyclooxygenase pathway, which makes it possible to transform arachidonic acid to PGG2 and then PGH2. Recent work on the cloning and sequencing of cyclooxygenase has revealed the presence of two isoenzymes, namely cyclooxygenase-1 (COX-1) and cyclooxygenase-2 (COX-2), in several species and particularly in man. The first is a constitutive enzyme which is expressed in the majority of tissues, while the second, which is expressed in a few tissues such as the brain, is inducible in the majority of tissues by numerous products, in particular by the cytokines and the mediators produced during the inflammatory reaction. Each enzyme has a different role and the inhibition of COX-1 or COX-2 will not have identical consequences. The inhibition of COX-1 will cause a decrease in the prostaglandins participating in homeostasis which can give rise to side effects. The inhibition of COX-2 will cause a decrease in the prostaglandins produced in an inflammatory situation. Thus the selective inhibition of COX-2 makes it possible to obtain a well-tolerated anti-inflammatory.

The compounds of the invention make it possible to achieve this selective inhibition. The compounds in question consequently have a very valuable pharmacological profile insofar as they possess anti-inflammatory and analgesic properties while being remarkably well tolerated, especially in gastric terms. They will be particularly indicated in the treatment of inflammatory phenomena and in the treatment of pain.

An example of their use which may be mentioned is the treatment of arthritis, especially rheumatoid arthritis, spondylitis, gouty arthritis, osteoarthritis, juvenile arthritis, autoimmune diseases and lupus erythematosus. They will also be indicated in the treatment of bronchial asthma, dysmenorrhea, tendinitis, bursitis, dermatological inflammations such as psoriasis, eczema, burns and dermatitis. They can also be used in the treatment of gastrointestinal inflammations, Crohn's disease, gastritis and ulcerative colitis, in the prevention of cancer, especially adenocarcinoma of the colon, in the prevention of neurodegenerative diseases, particularly Alzheimer's disease, in the prevention of stroke and epilepsy, and in the prevention of premature labour.

Their analgesic properties also enable them to be used for any pain symptoms, especially in the treatment of myalgia, articular pain or neuralgia, dental pain, herpes zoster and migraine, in the treatment of rheumatic complaints and pain of cancerous origin, and also as complementary treatments for infectious and febrile states.

The present invention further relates to the method for the preparation of the said products and to their application in therapeutics.

These diarylmethylene derivatives are characterised in that they have the general formula (I):

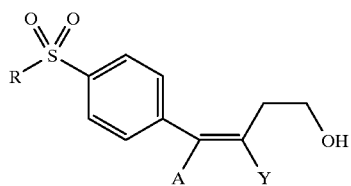

Formula (I)

in which:
R represents:
  a lower alkyl radical having from 1 to 6 carbon atoms,
  a lower haloalkyl radical having from 1 to 6 carbon atoms,
  an —$NH_2$ group,
A represents:
  an aromatic ring:

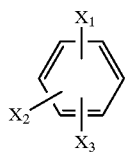

in which $X_1$, $X_2$ and $X_3$ independently represent:
  a hydrogen atom,
  a halogen atom,
  a lower alkyl radical having from 1 to 6 carbon atoms,
  a lower O-alkyl radical having from 1 to 6 carbon atoms,
  a trifluoromethyl radical,
  or even two of these can form together a methylene dioxy group,
A can also represent a thiophene or pyridine heterocycle

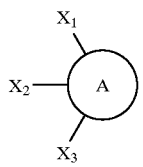

in which $X_1$, $X_2$ and $X_3$ have the same meanings as above,
Y represents:
  a —$CO_2R_1$ group in which $R_1$ is a hydrogen atom or a lower alkyl radical having from 1 to 6 carbon atoms,
  a —$CH_2OH$ group as well as their addition salts, in particular their pharmaceutically acceptable addition salts.

In the description and the claims, <<lower alkyl>> is understood as meaning a linear or branched hydrocarbon chain having from 1 to 6 carbon atoms. A lower alkyl radical is for example a methyl, ethyl, propyl, isopropyl, butyl, isobutyl, tertbutyl, pentyl, isopentyl, hexyl or isohexyl radical.

<<Lower haloalkyl radical>> is understood as meaning an alkyl radical having from 1 to 6 carbon atoms of which 1 to 7 hydrogen atoms have been substituted with 1 to 7 halogen atoms. A lower haloalkyl radical is for example a trifluoromethyl radical, a 2,2,2-trifluoroethyl radical, a pentafluoroethyl radical, a 2,2-difluoro-3,3,3-trifluoropropyl radical, a heptafluoropropyl radical, a chloromethyl or a bromomethyl radical.

<<Halogen>> is understood as meaning a chlorine, bromine, iodine or fluorine atom.

The derivatives according to the invention are advantageously the derivatives of formula (I) above in which:

R represents:
   a methyl radical,
   an —NH₂ group,

A represents an aromatic ring:

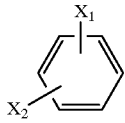

in which X₁ and X₂ independently represent:
   a hydrogen atom,
   a halogen atom,
   a lower O-alkyl radical having from 1 to 6 carbon atoms,
   a lower alkyl radical having from 1 to 6 carbon atoms, Y represents:
   a —CO₂R₁ group in which R₁ is a hydrogen atom or a lower alkyl radical having from 1 to 6 carbon atoms, or
   a CH₂OH group.

Within the framework of the present invention, it will be advantageous to use a compound of formula (I) in which at least one of the following conditions is satisfied:

R represents a methyl radical or an —NH₂ group,
A represents an aromatic ring:

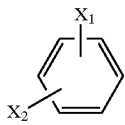

in which X₁ represents a chlorine or fluorine atom and X₂ represents a hydrogen atom or a chlorine atom,
Y represents a —COOC₂H₅ group or a —COOH group which can be salified.

The particularly preferred compounds of the invention are those which are selected from the following compounds:

Ethyl (Z)-3-(3,5-dichlorophenyl)-3-(4-methanesulphonylphenyl)-2-(2-hydroxyethyl)prop-2-enoate

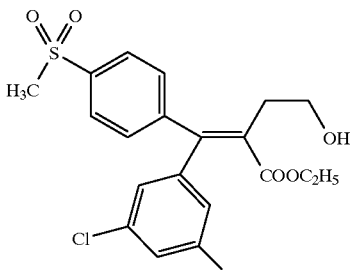

Sodium (E)-3-(4-fluorophenyl)-3-(4-methanesulphonylphenyl)-2-(2-hydroxyethyl)prop-2-enoate

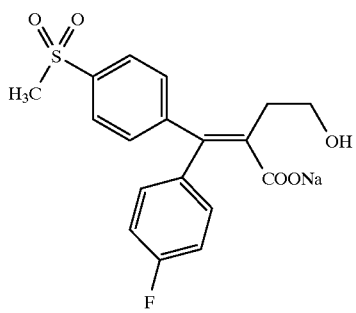

(E)-3-(4-fluorophenyl)-3-(4-sulphamoylphenyl)-2-(2-hydroxyethyl)prop-2-enoic acid

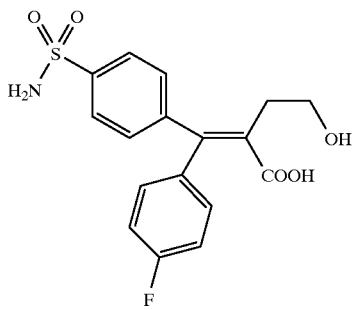

Sodium (Z)-3-(4-chlorophenyl)-3-(4-methanesulphonylphenyl)-2-(2-hydroxyethyl)prop-2-enoate

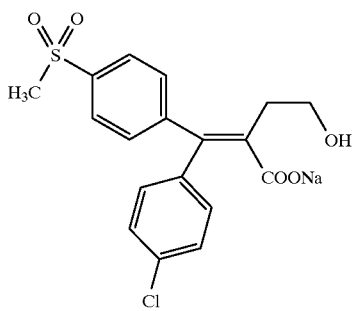

According to the invention, the compounds of formula (I) can be synthesised in the following way:

By a Friedel-Crafts reaction of the acid chloride of formula (II)

A—COCl     Formula (II)

in which A is defined as above, with an alkylthiophenol or a haloalkylthiophenol of formula:

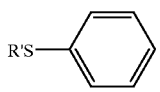

in which R' is a lower alkyl or lower haloalkyl radical, the ketones of formula (III)

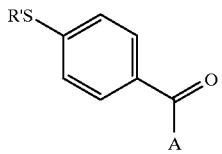

Formula (III)

in which A and R' are defined as above, are obtained.

The treatment of these ketones with an oxidising agent such as, for example meta-chloroperbenzoic acid or sodium perborate, gives the compounds of formula (IV):

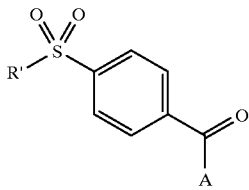

Formula (IV)

in which A and R' are defined as above.

The treatment of these ketones of formula (IV) with a succinic acid ester of formula $R'_1OOCCH_2CH_2COOR'_1$, in which $R'_1$ is a lower alkyl radical having from 1 to 6 carbon atoms, according to the Stobbe reaction in tert-butanol in the presence of sodium or potassium tert-butoxide or other sodium or potassium alkoxide, or even in toluene in the presence of sodium hydride, gives a mixture of two stereoisomers of formulae (V) and (V'):

Formula (V)

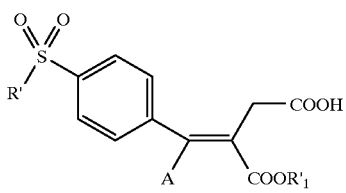

Formula (V')

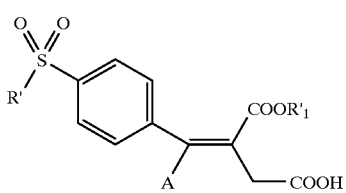

in which A, R' and $R'_1$ are defined as above.

These two stereoisomers can be separated by fractional recrystallisation of the mixture or by fractional recrystallisation of a salt of the acid, such as a sodium salt, a potassium salt or an amine salt, in particular an optically active amine such as R-(+)-1-phenylethylamine or S-(−)-1-phenylethylamine.

The choice of the basic condensation agent and solvent in which the Stobbe reaction takes place can also drive this reaction preferentially towards the Z isomer or the E isomer.

The selective reduction of the acid function of the products of formula (V) thus separated, for example by the action of borane or one of its complexes such as the borane/dimethyl sulphide complex, or even by the action of borane prepared in situ by the action of an acid on a sodium or potassium borohydride in a solvent such as tetrahydrofuran, glyme, diglyme or triglyme, gives the alcohol esters of formula (I):

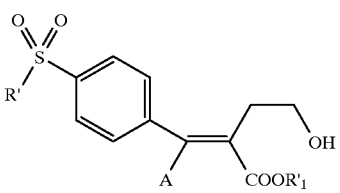

in which A and R' are defined as above.

The hydrolysis of the ester function with sodium hydroxide in refluxing ethanol for example, gives the derivatives of formula (I):

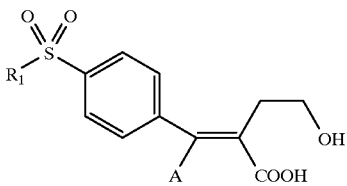

in which A and R' are defined as above.

The compounds of formula (I) in which R is an —$NH_2$ group can be prepared according to the following reaction scheme, in which Ph represents a phenyl group, $R'_1$ is defined as above and Z represents an MgBr radical when A is a ring derived from phenyl or thiophene and Z represents Li when A is a ring derived from pyridyl:

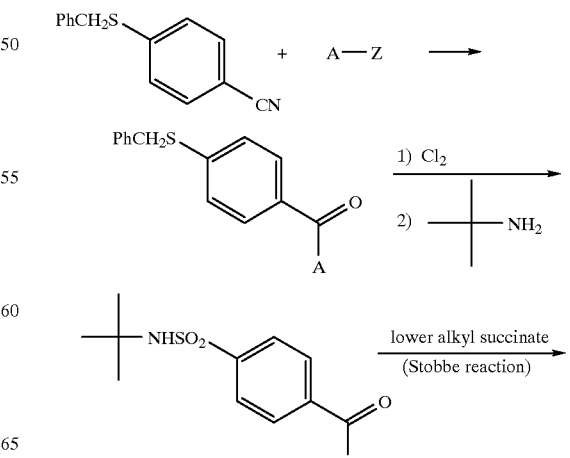

-continued

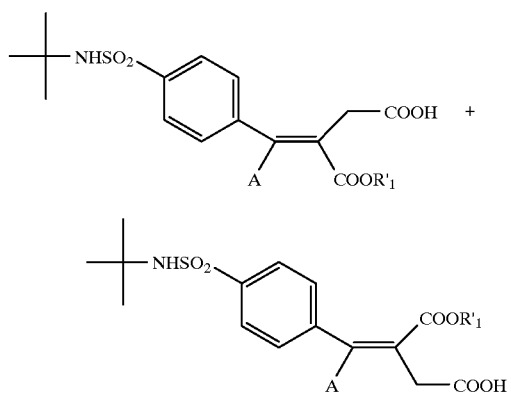

The compounds of formula (VI) are separated and reduced in the same way as the compounds of formula (V) which leads to the compounds of formula (VII):

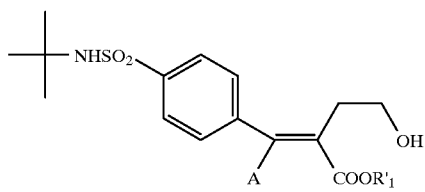

Formula (VII)

in which A and R'₁ are defined as above, the compounds of formula (VII) are treated with trifluoroacetic acid under reflux to give the lactone derivatives of formula (VIII):

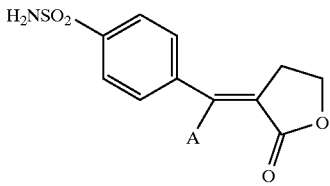

Formula (VIII)

in which A is defined as above.

The compounds of formula (VIII) are hydrolysed in basic medium to give the compounds of formula (I) in which R represents a $NH_2$ group and Y a COOH group.

The compounds of the invention of formula (I) in which R represents an $NH_2$ group can also be obtained from corresponding derivatives of formula (I) in which A and Y are defined as above and R represents a methyl group by any of the methods of transforming a methanesulphone group into a sulphonamide group known in the literature such as, for example, that described in Tetrahedron Letters, 1994, 39 (35), 7201 and which consists in reacting the methanesulphones with a base and a trialkylborane in an organic solvent such as tetrahydrofuran under reflux followed by the action of hydroxylamine O-sulphonic acid.

The compounds of formula (I) in which Y represents a $—COOR_1$ group can be obtained from the corresponding derivatives in which Y represents a —COOH group by esterification according to known methods, for example by the treatment with an alcohol under reflux in the presence of hydrogen chloride gas.

The compounds of formula (I) in which Y represents a $—CH_2OH$ group can be obtained from corresponding compounds of formula (I) in which Y represents a $—COOR_1$ group, by reduction according to the methods known to the person skilled in the art, such as, for example the action of a borohydride or lithium aluminium hydride in tetrahydrofuran, an implementation variant consisting in hydrolysing the ester function of the acid ester of formula (V) in a basic medium, and reducing the diacid obtained with borane or one of its complexes.

The compounds of formula (I) such as defined above as well as their addition salts, in particular their pharmaceutically acceptable addition salts, are cyclooxygenase-2 inhibitors and possess a very good anti-inflammatory and analgesic activity coupled with an excellent tolerance, particularly gastric tolerance.

These properties justify their application in therapeutics and the invention further relates, by way of drugs, to the products as defined by formula (I) above as well as their addition salts, in particular their pharmaceutically acceptable addition salts.

The addition salts of certain compounds of formula (I), in particular those which have an acid function, can be obtained by the reaction of these compounds with a base or with an amino acid according to a method known per se. Amongst the bases which can be used, sodium hydroxide, potassium hydroxide, potassium or sodium carbonate and sodium or potassium bicarbonate can be mentioned, and amongst the amino acids, lysine for example.

Thus, the invention also covers a pharmaceutical composition characterised in that it comprises a pharmaceutically effective amount of at least one compound of formula (I) such as defined above or one of its pharmaceutically acceptable addition salts incorporated in a pharmaceutically acceptable excipient, vehicle or carrier.

These compositions can be administered by the buccal, rectal, parenteral, transdermal, ocular, nasal or auricular route.

These compositions can be solid or liquid and can be presented in the pharmaceutical forms commonly used in human medicine, for example simple or coated tablets, gelatine capsules, granules, suppositories, injectable preparations, transdermal systems, eye drops, aerosols and sprays, and ear drops. They are prepared by the customary methods. The active principle, which consists of a pharmaceutically effective amount of at least one compound of formula (I) as defined above or one of its pharmaceutically acceptable addition salts can be incorporated therein together with excipients normally employed in pharmaceutical compositions, such as talc, gum arabic, lactose, starch, magnesium stearate, polyvidone, cellulose derivatives, cocoa butter, semi-synthetic glycerides, aqueous or non-aqueous vehicles, fats of animal or vegetable origin, glycols, various wetting agents, dispersants or emulsifiers, silicone gels, certain polymers or copolymers, preservatives, flavourings and colours.

The invention also covers a pharmaceutical composition with anti-inflammatory and analgesic activity which can be used especially as a favourable treatment for inflammatory phenomena and pain, said composition being characterised in that it comprises a pharmaceutically effective amount of at least one compound of formula (I) above or one of its pharmaceutically acceptable addition salts incorporated in a pharmaceutically acceptable excipient, vehicle or carrier.

In one embodiment, a pharmaceutical composition with anti-inflammatory and analgesic activity is prepared which may be used especially as a favourable treatment for various inflammations and pain.

The invention also covers a pharmaceutical composition useful in the prevention of cancer, in particular adenocarcinoma of the colon, in the prevention of neurodegenerative diseases, particularly Alzheimer's disease, in the prevention of stroke and epilepsy, and in the prevention of premature labour.

In one implementation variant, a composition is formulated as gelatine capsules or tablets containing a dose of 1 mg to 1000 mg, or as injectable preparations containing a dose of 0.1 mg to 500 mg. It is also possible to use compositions formulated as suppositories, ointments, creams, gels, aerosol preparations, transdermal preparations or plasters.

The invention also covers a method of therapeutic treatment for mammals, characterised in that a therapeutically effective amount of at least one compound of formula (I) as defined above or one of its pharmaceutically acceptable addition salts is administered to the said mammal. In one variant of this method of treatment, the compound of formula (I) either by itself or in association with a pharmaceutically acceptable excipient, is formulated as gelatine capsules or tablets containing a dose of 1 mg to 1000 mg for oral administration, as injectable preparations containing a dose of 0.1 mg to 500 mg or as suppositories, ointments, creams, gels or aerosol preparations.

This method affords especially a favourable treatment for inflammatory phenomena and pain.

In human and animal therapeutics, the compounds of formula (I) can be administered by themselves or in association with a physiologically acceptable excipient, in any form, in particular orally in the form of gelatine capsules or tablets, or parenterally in the form of injectable solutions. It is possible to envisage other forms of administration such as suppositories, ointments, creams, gels or aerosol preparations.

As will be clearly apparent from the pharmacological experiments given at the end of the description, the compounds according to the invention can be administered in human therapeutics, in the above-mentioned indications, orally in the form of tablets or gelatine capsules containing a dose of 1 mg to 1000 mg, or parenterally in the form of injectable preparations containing a dose of 0.1 mg to 500 mg, in one or more daily dosage units, for an adult with an average weight of 60 to 70 kg.

In animal therapeutics, the daily dose which can be used is between 0.1 mg and 100 mg per kg.

Further characteristics and advantages of the invention will be understood more clearly by reading the following Examples, which in no way imply a limitation but are given by way of illustration.

EXAMPLE 1

4-chloro-4'-methylthiobenzophenone

Formula (III): A=4-chlorophenyl, R'=CH$_3$

To a solution of 105.8 g (0.852 mole) of thioanisole and 156.52 g (0.894 mole) of 4-chlorobenzoyl chloride in 600 ml of dichloromethane, are added 130.6 g (0.980 mole) of aluminium chloride in maintaining the temperature between 0° C. and 5° C. The mixture is then stirred for 2 hours at room temperature, left to stand overnight and then heated under reflux for 6 hours. After cooling, the mixture is poured into an iced solution of dilute hydrochloric acid. After separation, the aqueous phase is washed with dichloromethane and the organic phases are combined, dried over magnesium sulphate and evaporated in vacuo to give 196.8 g of 4-chloro-4'-methylthiobenzophenone as crystals with a melting point of 134° C.

EXAMPLE 2

4-chloro-4'-methanesulphonylbenzophenone

Formula (IV): A=4-chlorophenyl, R'=CH$_3$

To a solution of 40 g (0.152 mole) of 4-chloro-4'-methylthiobenzophenone, prepared in example 1, in 700 ml of dichloromethane, are added 82.6 g (0.335 mole) of 70% 3-chloroperbenzoic acid in maintaining the temperature at less than 5° C. The mixture is then stirred at room temperature for 4 hours and the crystals are filtered off. The filtrate is washed with sodium carbonate solution, dried over magnesium sulphate and evaporated in vacuo to give 42.5 g of 4-chloro-4'-methanesulphonylbenzophenone as crystals with a melting point of 176° C.

EXAMPLE 3

(Z)-3-ethoxycarbonyl-4-(4-chlorophenyl)-4-(4-methanesulphonyl-phenyl)but-3-enoic acid Formula (V) A=4-chlorophenyl, R'=CH$_3$, R'$_1$ =C$_2$H$_5$ 341.5 g (1.16 moles) of 4-chloro-4'-methanesulphonylbenzophenone, prepared in example 2, 310 ml (1.85 moles) of ethyl succinate and 195.5 g (1.74 moles) of potassium t-butoxide are successively added to 2.5 litres of t-butanol. The temperature rises to 40–45° C., the mixture is stirred for 7 hours at room temperature after this exothermic reaction and is then poured into iced water. After acidification to pH 3 with hydrochloric acid, the mixture is extracted with diethyl ether. The organic phase is washed with water, dried over magnesium sulphate and evaporated in vacuo. The oil obtained is dissolved in diethyl ether and then left overnight at room temperature. The crystals formed are filtered off and dried to provide 102 g of (Z)-3-ethoxycarbonyl-4-(4-chlorophenyl)-4-(4-methanesulphonylphenyl)but-3-enoic acid as crystals with a melting point of 184–186° C. after recrystallisation from isopropanol. The evaporation of the filtrate allows the recovery of 219 g of a mixture consisting of 82% of the (E)-isomer and 18% of the (Z)-isomer.

EXAMPLE 4

Ethyl (Z)-3-(4-chlorophenyl)-3-(4-methanesulphonylphenyl)-2-(2-hydroxyethyl)prop-2-enoate Formula (I): R=CH$_3$; A=4-chlorophenyl; Y=CO$_2$Et To a solution of 32.8 g (0.0775 mole) of (Z)-3-ethoxycarbonyl-4-(4-chlorophenyl)-4-(4-methanesulphonylphenyl)but-3-enoic acid, prepared in example 3, in 90 ml of anhydrous tetrahydrofuran are added dropwise 15.5 ml (0.155 mole) of borane/dimethyl sulphide complex. The mixture is stirred at room temperature for 8 hours and 23.5 ml of methanol are added dropwise. The mixture is evaporated to dryness in vacuo and the residue is dissolved in ethyl acetate. After washing with potassium carbonate solution, the organic phase is separated, dried over magnesium sulphate and evaporated in vacuo to give 30.8 g of ethyl (Z)-3-(4-chlorophenyl)-3-(4-methanesulphonylphenyl)-2-(2-hydroxyethyl)prop-2-enoate

EXAMPLE 5

Sodium (Z)-3-(4-chlorophenyl)-3-(4-methanesulphonylphenyl)-2-(2-hydroxyethyl)prop-2-enoate Formula (I): R=CH$_3$; A=4-chlorophenyl; Y=CO$_2$H To a solution of 5 g (0.0122 mole) of ethyl (Z)-3-(4-chlorophenyl)-3-(4-methanesulphonylphenyl)-2-(2-hydroxyethyl)prop-2-enoate, prepared in example 4, in 10 ml of ethanol are added 11 ml (0.011 mole) of 1 M sodium hydroxide. The mixture is heated for 2 hours under reflux, then evaporated to dryness in vacuo. The crystals obtained are washed with ethyl acetate and with diethyl ether and then dried to provide 4.5 g of sodium (Z)-3-(4-chlorophenyl)-3-(4-methanesulphonylphenyl)-2-(2-hydroxyethyl)prop-2-enoate as crystals with melting point of 257–259° C.

EXAMPLE 6

4-fluoro-4'-methylthiobenzophenone

Formula (III): A=4-fluorophenyl; R'=CH$_3$
Prepared according to the method of example 1.
Crystals with a melting point of 88° C.

EXAMPLE 7

4-fluoro-4'-methanesulphonylbenzophenone

Formula (IV): A=4-fluorophenyl; R'=CH$_3$.
Prepared according to the method of example 2.
Crystals with a melting point of 136° C.

EXAMPLE 8

(E)-3-ethoxycarbonyl-4-(4-fluorophenyl)-4-(4-methanesulphonyl-phenyl)but-3-enoic acid Formula (V): A=4-fluorophenyl; R'=CH$_3$; R'$_1$C$_2$H$_5$
Prepared according to the method of example 3.
Crystals with a melting point of 155–156° C.

EXAMPLE 9

Ethyl (E)-3-(4-fluorophenyl)-3-(4-methanesulphonylphenyl)-2-(2-hydroxyethyl)prop-2-enoate Formula (I): R=CH$_3$; A=4-fluorophenyl; Y=CO$_2$Et Prepared according to the method of example 4.
Crystals with a melting point of 100° C.

EXAMPLE 10

Sodium (E)-3-(4-fluorophenyl)-3-(4-methanesulphonylphenyl)-2-(2-hydroxyethyl)prop-2-enoate Formula (I): R=CH$_3$; A=4-fluorophenyl; Y=CO$_2$H
Prepared according to the method of example 5.
Crystals with a melting point of 268–269° C.

EXAMPLE 11

3,5-dichloro-4'-methylthiobenzophenone

Formula (III): A=3,5-dichlorophenyl; R'=CH$_3$
Prepared according to the method of example 1.
Crystals with a melting point of 108° C.

EXAMPLE 12

3,5-dichloro-4'-methanesulphonylbenzophenone

Formula (IV): A=3,5-dichlorophenyl; R'=CH$_3$.
Prepared according to the method of example 2.
Crystals with a melting point of 200° C.

EXAMPLE 13

(Z)-3-ethoxycarbonyl-4-(3,5-dichlorophenyl)-4-(4-methanesulphonylphenyl)but-3-enoic acid Formula (V): A=3,5-dichlorophenyl; R'=CH$_3$; R'$_1$=C$_2$H$_5$
Prepared according to the method of example 3.
Crystals with a melting point of 178° C.

EXAMPLE 14

Ethyl (Z)-3-(3,5-dichlorophenyl)-3-(4-methanesulphonylphenyl)-2-(2-hydroxyethyl)prop-2-enoate Formula (I): R=CH$_3$; A=3,5-dichlorophenyl; Y=CO$_2$Et
Prepared according to the method of example 4.
Crystals with a melting point of 130° C.

EXAMPLE 15

Sodium (Z)-3-(3,5-dichlorophenyl)-3-(4-methanesulphonylphenyl)-2-(2-hydroxyethyl)prop-2-enoate Formula (I): R=CH$_3$; A=3,5-dichlorophenyl; Y=CO$_2$H
Prepared according to the method of example 5.
Crystals with a melting point of 207–209° C.

EXAMPLE 16

4-benzylthiobenzonitrile

A mixture of 37.2 g of benzylmercaptan, 36.3 g of 4-fluorobenzonitrile and 42 g of potassium carbonate in 700 ml of butan-2-one is held under reflux for 7 hours. The solvent is evaporated in vacuo, the residue is taken up into water and petroleum ether. The crystals formed are filtered off, washed with water and petroleum ether to give 46 g of 4-benzylthiobenzonitrile as crystals with a melting point of 85° C.

EXAMPLE 17

4-benzylthio-4'-fluorobenzophenone

To a suspension of 9.6 g of magnesium turnings in 20 ml of anhydrous diethyl ether is added dropwise a solution of 44 ml of 4-bromo-1-fluorobenzene in 300 ml of anhydrous diethyl ether. At the end of the addition, the mixture is stirred for a few minutes at room temperature and a solution of 46 g of 4-benzylthiobenzonitrile, prepared in example 16, in 400 ml of anhydrous tetrahydrofuran is added dropwise. The diethyl ether is distilled off and the mixture is heated under reflux for 3 hours before being cooled with ice. A 6 M solution of hydrochloric acid (400 ml) is added dropwise and the mixture is heated under reflux for 6 hours. After the addition of water and dichloromethane, the organic phase is separated, dried over magnesium sulphate and evaporated in vacuo. The residue crystallises in diisopropyl ether to give 48 g of 4-benzylthio-4'-fluorobenzophenone as crystals with a melting point of 96° C.

EXAMPLE 18

4-(1,1-dimethylethyl)sulphamoyl-4'-fluorobenzophenone

Chlorine is bubbled into a solution of 43 g of 4-benzylthio-4'-fluorobenzophenone, prepared in example 17, in 300 ml of acetic acid cooled to 0° C., until saturation (36 g). The mixture is then stirred for two hours at room temperature and then poured into iced water and extracted with dichloromethane. The organic phase is washed with water, dried over magnesium sulphate and evaporated in vacuo to give 47 g of an oil which is dissolved in 100 ml of 1,2-dichloroethane. This solution is added dropwise to a solution of 50 ml of t-butylamine in 300 ml of 1,2-dichloroethane. The mixture is heated for one hour at 80° C., cooled and washed with water then with dilute hydrochloric acid. The organic phase is dried over magnesium sulphate and evaporated in vacuo. The residue crystallises in diethyl ether to give 25 g of 4-(1,1-dimethylethyl)sulphamoyl-4'-fluorobenzophenone as crystals with a melting point of 160° C.

EXAMPLE 19

(E)-3-ethoxycarbonyl-4-(4-(1,1-dimethylethyl)sulphamoylphenyl)-4-(4-fluorophenyl)but-3-enoic acid Formula (VI): A=4-fluorophenyl, $R'_1=C_2H_5$ Prepared according to the method of example 3, using two equivalents of potassium tert-butoxide.

Amorphous powder used as such in the next step.

EXAMPLE 20

Ethyl (E)-3-(4-(1,1-dimethylethyl)sulphamoylphenyl)-3-(4-fluorophenyl)-2-(2-hydroxyethyl)prop-2-enoate Formula (VII): A=4-flurophenyl, $R'_1=C_2H_5$ Prepared according to the method of example 4.

Oil used as such in the next step.

EXAMPLE 21

(E)-3-[1-(4-sulphamoylphenyl)-1-(4-fluorophenyl)methylene]-dihydrofuran-2-one

Formula (VIII): A=4-fluorophenyl

A solution of 10 g of ethyl (E)-3-(4-(1,1-dimethylethyl)sulphamoylphenyl)-3-(4-fluorophenyl)-2-(2-hydroxyethyl)prop-2-enoate, prepared in example 20, in 50 ml of trifluoroacetic acid is heated under reflux for 16 hours. The solution is evaporated to dryness in vacuo and the residue is taken up into an acetone/diethyl ether mixture. The crystals formed are filtered off and dried to give 5.1 g of (E)-3-[1-(4-sulphamoylphenyl)-1-(4-fluorophenyl)methylene]-dihydrofuran-2-one as crystals with a melting point of 202° C.

EXAMPLE 22

(E)-3-(4-sulphamoylphenyl)-3-(4-fluorophenyl)-2-(2-hydroxyethyl)prop-2-enoic acid Formula (I): R=NH$_2$, A=4-fluorophenyl, Y=CO$_2$H Prepared according to the method of example 5 from (E)-3-[1-(4-sulphamoylphenyl)-1-(4-fluorophenyl)methylene]-dihydrofuran-2-one, prepared in example 21. The sodium salt obtained is treated with dilute hydrochloric acid and is extracted with dichloromethane, the solvent is evaporated in vacuo to give (E)-3-(4-sulphamoylphenyl)-3-(4-fluorophenyl)-2-(2-hydroxy-ethyl)prop-2-enoic acid as crystals with a melting point of 160–162° C.

EXAMPLE 23

3,4-dichloro-4'-methylthiobenzophenone

Formula (III): A=3,4-dichlorophenyl, R'=CH$_3$

Prepared according to the method of example 1.

Crystals with a melting point of 108° C.

EXAMPLE 24

3,4-dichloro-4'-methanesulphonylbenzophenone

Formula (IV): A=3,4-dichlorophenyl, R'=CH$_3$

Prepared according to the method of example 2.

Crystals with a melting point of 148° C.

EXAMPLE 25

(Z)-3-ethoxycarbonyl-4-(3,4-dichlorophenyl)-4-(4-methanesulphonylphenyl)but-3-enoic acid Formula (V): A=3,4-dichlorophenyl, R'=CH$_3$, $R'_1=C_2H_5$ Prepared according to the method of example 3.

Oil used as such in the next step.

EXAMPLE 26

Ethyl (Z)-3-(3,4-dichlorophenyl)-3-(4-methanesulphonylphenyl)-2-(2-hydroxyethyl)prop-2-enoate Formula (I): R=CH$_3$, A=3,4-dichlorophenyl, Y=CO$_2$Et Prepared according to the method of example 4.

Oil used as such in the next step.

EXAMPLE 27

Sodium (Z)-3-(3,4-dichlorophenyl)-3-(4-methanesulphonylphenyl)-2-(2-hydroxyethyl)prop-2-enoate Formula (I): R=CH$_3$, A=3,4-dichlorophenyl, Y=CO$_2$H Prepared according to the method of example 5.

Crystals with a melting point of 264–266° C.

EXAMPLE 28

(Z)-2-[1-(4-chlorophenyl)-1-(4-methanesulphonylphenyl)methylene]succinic acid

Formula (V): A=4-chlorophenyl, R'=CH$_3$, $R'_1=H$

To a suspension of 50 g (0.118 mole) of (Z)-3-ethoxycarbonyl-4-(4-chlorophenyl)-4-(4-methanesulphonylphenyl)-3-butenoic acid, prepared in example 3, in 1000 ml of ethanol is added a solution of 10.4 g (0.26 mole) of sodium hydroxide in 25 ml of water. The mixture is heated under reflux for 6 hours, the precipitate is filtered off and washed with ethanol. The solid is then taken up into 500 ml of a 1N sodium hydroxide solution and the insoluble is filtered off. The aqueous phase is washed with dichloromethane and then acidified with hydrochloric acid to pH=1. After one hour's stirring, the precipitate obtained is filtered under suction, washed with water and dried to give 38.4 g of (Z)-2-[1-(4-chlorophenyl)-1-(4-methanesulphonylphenyl)-methylene]succinic acid in the form of crystals with a melting point of 199–200° C.

EXAMPLE 29

(Z)-2-[1-(4-chlorophenyl)-1-(4-methanesulphonylphenyl)methylene]-1,4-butanediol

Formula (I): R=$CH_3$, A=4-chlorophenyl, Y=$CH_2OH$

To a solution of 7.85 g (0.0199 mole) of (Z)-2-[1-(4-chlorophenyl)-1-(4-methanesulphonylphenyl)methylene] succinic acid, prepared in example 28, in 40 ml of tetrahydrofuran are added dropwise 5.65 ml (0.0596 mole) of borane/dimethyl sulphide complex. The mixture is then stirred for 3 hours at ambient temperature and then 1 hour at 50° C. After returning to ambient temperature, 5 ml of ethanol are added dropwise. The mixture is then concentrated to half its volume and then taken up into water. The crystals obtained are filtered off under suction and washed with pentane and dried giving 6.92 g of (Z)-2-[1-(4-chlorophenyl)-1-(4-methanesulphonylphenyl)-methylene]-1,4-butanediol in the form of crystals with a melting point of 159–160° C.

EXAMPLE 30

3-chloro-4-methoxy-4'-methylthiobenzophenone

Formula (III): 3-chloro-4-methoxyphenyl, R'=$CH_3$

Prepared according to the method of example 1 from 3-chloro-4-methoxybenzoyl chloride.

Crystals with a melting point of 100° C.

EXAMPLE 31

3-chloro-4-methoxy-4'-methanesulphonylbenzophenone

Formula (IV): A=3-chloro-4-methoxyphenyl, R'=$CH_3$
Crystals with a melting point of 164° C.

EXAMPLE 32

(Z)-3-ethoxycarbonyl-4-(3-chloro-4-methoxyphenyl)-4-(4-methanesulphonylphenyl)-3-butenoic acid Formula (V): A=3-chloro-4-methoxyphenyl, R'=$CH_3$, $R'_1$=$C_2H_5$ Prepared according to the method of example 3.
Crystals with a melting point of 179° C.

EXAMPLE 33

Ethyl (Z)-3-(3-chloro-4-methoxyphenyl)-3-(4-methanesulphonylphenyl)-2-(2-hydroxyethyl)-2-propenoate Formula (I): R=$CH_3$, A=3-chloro-4-methoxyphenyl, Y=$CO_2Et$ Prepared according to the method of example 4.
Crystals with a melting point of 102° C.

EXAMPLE 34

4-benzylthio-3'-methylbenzophenone

Prepared according to the method of example 17 from 3-bromotoluene.

Crystals with a melting point of 95° C.

EXAMPLE 35

4-(1,1-dimethylethyl)sulphamoyl-3'-methylbenzophenone

Prepared according to the method of example 18 from 4-benzylthio-3'-methylbenzophenone prepared in example 34.

Crystals with a melting point of 144° C.

EXAMPLE 36

3-ethoxycarbonyl-4-(4-(1,1-dimethylethyl) sulphamoylphenyl)-4-(3-methylphenyl)-3-butenoic acid Formula (VI): A=3-methylphenyl, $R'_1$=$C_2H_5$
Prepared according to the method of example 19.
Mixture of (E) and (Z) isomers in the form of an oil used as such in the next step.

EXAMPLE 37

Ethyl 3-(4-(1,1-dimethylethyl)sulphamoylphenyl)-3-(3-methylphenyl)-2-propenoate

Formula (VII): A=3-methylphenyl, $R'_1$=$C_2H_5$
Prepared according to the method of example 20.
Mixture of (Z) and (E) isomers in the form of an oil used as such in the next step.

EXAMPLE 38

(Z)-3-[1-(4-sulphamoylphenyl)-1-(3-methylphenyl) methylene]-dihydrofuran-2-one

Formula (VIII): A=3-methylphenyl
Prepared according to the method of example 21.
The mixture of (Z) and (E) isomers is chromatographed on silica eluting with dichloromethane/acetone (10/1) to give the (Z) isomer in the form of crystals with a melting point of 161° C.

EXAMPLE 39

(Z)-3-(4-sulphamoylphenyl)-3-(3-methylphenyl)-2-(2-hydroxyethyl)-2-propenoic acid Formula (I): R=$NH_2$, A=3-methylphenyl, Y=$CO_2H$
Prepared according to the method of example 22.
Crystals with a melting point of 117–118° C.

EXAMPLE 40

4-benzylthio-4'-methylbenzophenone

Prepared according to the method of example 17 from 4-bromotoluene.

Crystals with a melting point of 110° C.

EXAMPLE 41

4-(1,1-dimethylethyl)sulphamoyl-4'-methylbenzophenone

Prepared according to the method of example 18 from 4-benzylthio-4'-benzophenone prepared in example 40.

Crystals with a melting point of 120° C.

EXAMPLE 42

3-Ethoxycarbonyl-4-(4-(1,1-dimethylethyl) sulphamoylphenyl)-4-(4-methylphenyl)-3-butenoic acid Formula (VI): A=4-methylphenyl, $R'_1=C_2H5$
Prepared according to the method of example 19.
Mixture of (E) and (Z) isomers in the form of an oil used as such in the next step.

EXAMPLE 43

Ethyl 3-(4-(1,1-dimethylethyl)sulphamoylphenyl)-3-(4-methylphenyl)-2-(2-hydroxyethyl)-2-propenoate Formula (VII): A=4-methylphenyl, $R'_1=C_2H_5$
Prepared according to the method of example 20.
Mixture of (E) and (Z) isomers in the form of an oil used as such in the next step.

EXAMPLE 44

(Z)-3-[1-(4-sulphamoylphenyl)-1-(4-methylphenyl) methylene]-dihydrofuran-2-one

Formula (VIII): A=4-methylphenyl
Prepared according to the method of example 21.
The mixture of (Z) and (E) isomers is chromatographed on silica eluting with dichloromethane/acetone (10/1) giving the (Z) isomer in the form of crystals with a melting point of 159° C.

EXAMPLE 45

(Z)-3-(4-sulphamoylphenyl)-3-(4-methylphenyl)-2-(2-hydroxyethyl)-2-propenoic acid Formula (I): $R=NH_2$, A=4-methylphenyl, $Y=CO_2H$
Prepared according to the method of example 22.
Obtained in an amorphous form.

PHARMACOLOGY

The anti-inflammatory activity of the compounds of the Examples has been evaluated according to the method of oedema with carrageenan and the analgesic activity has been evaluated according to the method of arthritis with kaolin.
Methods
Anti-Inflammatory Activity The anti-inflammatory activity is evaluated in rats by the test of oedema with carrageenan. The product is administered orally at a rate of 2.5 ml/100 g (n=6 animals per dose) 2 hours 30 minutes after a water overload taken orally (2.5 ml/ 100 g). One hour after administration of the product, the oedema is induced by plantar subcutaneous injection of aqueous 2% carrageenan solution. The percentage inhibition of the volume of the oedema is calculated after 3 hours by measuring the volume of the paw with the aid of a mercury plethysmometer.
Analgesic Activity The analgesic activity is evaluated in rats by the test of arthritis with kaolin. Thirty minutes after intra-articular administration of an aqueous 10% suspension of kaolin, the product is administered orally at a rate of 1 ml/100 g (n=10 animals per dose). The percentage inhibition of the animal's pain response (by rating the way it walks) is calculated 5 hours 30 minutes after administration of the product.

| Example | Dose (mg/kg) | Anti-inflammatory activity % inhibition | Analgesic activity % inhibition |
|---|---|---|---|
| 14 | 30 | 28.9 ± 4.5 | 45.8 ± 10.9 |
| 27 | 100 | 32.4 ± 8.2 | 63.6 ± 13.2 |

Inhibition Of The COX-1 and COX-2 Enzymatic Activities

The molecule studied is preincubated for 10 minutes at 25° C. with 2 U of COX-1 (purified enzyme from ram seminal vesicles) or 1 U of COX-2 (purified enzyme from ewe placenta). Arachidonic acid (6 $\mu$M for COX-1, 4, $\mu$M for COX-2) is added to the reaction medium and incubation is carried out for 5 minutes at 25° C. When incubation has ended, the enzymatic reaction is stopped by the addition of 1 N HCl and the PGE2 produced is determined by EIA.

The results are expressed as the percentage inhibition of the COX-1 and COX-2 enzymatic activities and correspond to mean (±) standard deviations from the average of 4 determinations.

| | % inhibition of COX-2 activity | | % inhibition of COX-1 activity | |
|---|---|---|---|---|
| Example | $10^{-5}$M | $10^{-7}$M | $10^{-5}$M | $10^{-7}$M |
| 14 | 80 ± 2 | 16 ± 9 | 0 ± 0 | 0 ± 0 |

TOXICOLOGY

The first toxicology studies performed show that the products of the Examples do not induce a deleterious effect in the rat after the oral absorption of doses ranging up to 300 mg/kg.

We claim:
1. A 1,2 diarylmethylene compound of formula (I):

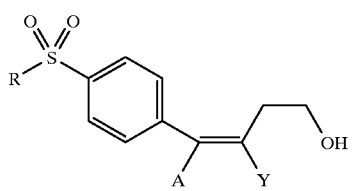

Formula (I)

wherein:

R is:
a lower alkyl radical having 1 to 6 carbon atoms,
a lower haloalkyl radical having 1 to 6 carbon atoms, or
an —$NH_2$ group,

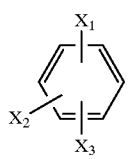

A is a thiophene or pyridine heterocycle

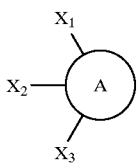

wherein $X_1$, $X_2$ and $X_3$ independently are:
- the hydrogen atom,
- a halogen atom,
- a lower alkyl radical having 1 to 6 carbon atoms,
- lower O-alkyl radical having 1 to 6 carbon atoms or
- a trifluoromethyl radical,
- or even two of these together form a methylene dioxy group, Y is:
- a $CO_2R_1$ group wherein $R_1$ is selected from the group consisting of the hydrogen atom and a lower alkyl radical having 1 to 6 carbon atoms,
- a —$CH_2OH$ group,
- or a pharmaceutically acceptable salt thereof.

2. A compound of formula (I) according to claim 1, wherein:

R is:
- a methyl radical, or
- an $NH_2$ group,

A is a thiophene or pyridine heterocycle

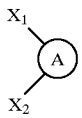

wherein $X_1$ and $X_2$ independently are
- a hydrogen atom,
- a halogen atom,
- a lower O-alkyl radical having from 1 to 6 carbon atoms, or
- a lower alkyl radical having from 1 to 6 carbon atoms, Y is
- a —$CO_2R_1$ group wherein $R_1$ is selected from the group consisting of a hydrogen atom or a lower alkyl radical having 1 to 6 carbon atoms, or
- a $CH_2OH$ group,
- or a pharmaceutically acceptable salt thereof.

3. A compound according to claim 1, wherein R is selected from the group consisting of a methyl group or an —$NH_2$ group.

4. A compound according to claim 1, wherein A is an aromatic ring:

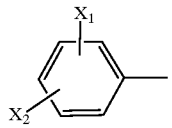

wherein $X_1$ is selected from the group consisting of a chlorine atom or a fluorine atom, and $X_2$ is selected from the group consisting of a hydrogen atom or a chlorine atom.

5. A compound according to claim 1, wherein Y is selected from the group consisting of the —$COOC_2H_5$ or the —COOH group and its salts.

6. A pharmaceutical composition, which comprises a pharmaceutically effective amount of at least one compound of formula (I) such as defined in claim 1, or a pharmaceutically acceptable salt thereof, incorporated in a pharmaceutically acceptable excipient, vehicle or carrier.

7. A pharmaceutical composition with anti-inflammatory and analgesic activity, which comprises a pharmaceutically effective amount of a compound of formula (I) as defined in claim 1, or a pharmaceutically acceptable salt thereof, incorporated in a pharmaceutically acceptable excipient, vehicle or carrier.

8. A pharmaceutical composition according to claim 6, which is presented in the form of gelatin capsules or tablets containing a dose of 1 mg to 1,000 mg.

9. A pharmaceutical composition according to claim 6, which is presented in the form of injectable preparations containing a dose of 0.1 mg to 500 mg.

* * * * *